(12) United States Patent
Piantoni et al.

(10) Patent No.: US 9,750,645 B2
(45) Date of Patent: Sep. 5, 2017

(54) METHOD AND MACHINE FOR MAKING ABSORBENT SANITARY ARTICLES

(71) Applicant: GDM S.p.A., Bologna (IT)

(72) Inventors: Matteo Piantoni, Albino (IT); Alberto Perego, Milan (IT)

(73) Assignee: GDM S.P.A., Bologna (IT)

( * ) Notice: Subject to any disclaimer, the term of this patent is extended or adjusted under 35 U.S.C. 154(b) by 73 days.

(21) Appl. No.: 14/438,831

(22) PCT Filed: Nov. 11, 2013

(86) PCT No.: PCT/IB2013/060058
§ 371 (c)(1),
(2) Date: Apr. 27, 2015

(87) PCT Pub. No.: WO2014/076626
PCT Pub. Date: May 22, 2014

(65) Prior Publication Data
US 2015/0257940 A1  Sep. 17, 2015

(30) Foreign Application Priority Data
Nov. 16, 2012  (IT) .............................. BO2012A0630

(51) Int. Cl.
*A61F 13/15*  (2006.01)

(52) U.S. Cl.
CPC .. *A61F 13/15756* (2013.01); *A61F 13/15723* (2013.01); *A61F 13/15764* (2013.01); *A61F 2013/15821* (2013.01)

(58) Field of Classification Search
CPC .......... A61F 13/15756; A61F 13/15723; A61F 13/15764; A61F 2013/15821
See application file for complete search history.

(56) References Cited

U.S. PATENT DOCUMENTS

| | | | |
|---|---|---|---|
| 5,705,013 A | 1/1998 | Nease et al. | |
| 8,679,282 B2* | 3/2014 | Piantoni | A61F 13/15756 |
| | | | 156/250 |

(Continued)

FOREIGN PATENT DOCUMENTS

| | | |
|---|---|---|
| EP | 2238955 | 10/2010 |
| WO | 2010001361 | 1/2010 |
| WO | 2011101772 | 8/2011 |

OTHER PUBLICATIONS

International Search Report dated Jan. 28, 2014 for related PCT Application No. PCT/IB2013/060058.

*Primary Examiner* — John C Hong
(74) *Attorney, Agent, or Firm* — Shuttleworth & Ingersoll, PLC; Timothy Klima

(57) ABSTRACT

In a method for making absorbent sanitary articles, each absorbent article includes a pair of side tabs fed from a single continuous tape divided by oblique cuts into first and second series of side tabs oriented in opposite directions. The side tabs of the first and second series are then fed along a first path and along a second path, respectively and are first rotated by 180° and then combined and transferred separately along a third, common path along which each tab of the first series has a respective tab of the second series placed alongside it to form a pair of side tabs. At least one of the side tabs of each pair is moved sideways such that each pair of side tabs is applied to a continuous web of material at a predetermined spacing.

20 Claims, 4 Drawing Sheets

(56) References Cited

U.S. PATENT DOCUMENTS

2004/0122413 A1  6/2004 Roessler et al.
2006/0271004 A1  11/2006 Petersen
2015/0297416 A1* 10/2015 Piantoni ............ A61F 13/15756
                                              156/517

* cited by examiner

METHOD AND MACHINE FOR MAKING ABSORBENT SANITARY ARTICLES

This application is the National Phase of International Application PCT/IB2013/060058 filed Nov. 11, 2013 which designated the U.S. and that International Application was published under PCT Article 21(2) in English.

This application claims priority to Italian Patent Application No. BO2012A000630 filed Nov. 16, 2012, which application is incorporated by reference herein.

TECHNICAL FIELD

This invention relates to a method and a machine for making absorbent sanitary articles.

More specifically, the invention relates to a method and a machine for making absorbent sanitary articles such as disposable nappies for children or adults.

BACKGROUND ART

As is known, these articles are obtained by laying a sheet of impermeable material over a sheet of permeable material (of non-woven fabric) and interposing an absorbent pad between the two sheets.

The absorbent article also comprise further accessory components, such as side tabs for fastening the nappy round the wearer's waist.

Generally, a prior art machine of this kind comprises a feed line for advancing a continuous web of material for making the absorbent articles and which is subsequently cut into the individual absorbent articles.

More specifically, the side tabs are applied to the continuous web along predetermined stretches so that when the web is cut, each absorbent article has at least one pair of side tabs.

Patent application WO2010001361A1, in the name of the same Applicant as this invention, describes a machine for making absorbent articles of the above mentioned kind.

The machine comprises a unit for forming pairs of side tabs and applying these pairs to the continuous web.

The unit comprises a device for cutting a continuous tape into individual side tabs, a first and a second roller, both located downstream of the cutting device, for picking up respective individual side tabs, and a roller, located downstream of the pickup rollers, for receiving the individual side tabs and capable of forming the pairs of side tabs which will be applied to the continuous web.

An accelerator roller picks up the pairs of side tabs from the receiving roller and conveys them in step to apply them to the continuous web.

In order to space the individual side tabs picked up from the continuous tape until they are positioned at a predetermined reciprocal distance based on the waistline of the absorbent articles, the first and second pickup rollers and the receiving roller are equipped with respective suction pads slidable along a direction parallel to the axis of rotation of the rollers.

More specifically, the first and the second pickup rollers initially translate the respective side tabs to position them at a distance which is smaller than the predetermined reciprocal distance based on the waistline, after which the receiving roller further spaces the side tabs of each pair until reaching that reciprocal distance.

This unit for forming and applying the side tabs has several disadvantages, however.

In effect, in order to meet market requirements for increasingly higher machine productivity, the need has arisen to increase the feed speed of the continuous web of nappies and, consequently, the speed of rotation of the rollers making up the unit for forming and applying the pairs of side tabs.

On account of the slidable suction pads, however, the first and second pickup rollers and the receiving roller are limited in their speed and cannot keep up with the high feed speed of the continuous web which the side tabs have to be applied to.

DISCLOSURE OF THE INVENTION

This invention has for an aim to provide a machine for making absorbent sanitary articles and whose productivity is higher than prior art machines.

The above mentioned technical purpose and aims are achieved by a method and a machine having technical features as disclosed herein.

BRIEF DESCRIPTION OF THE DRAWINGS

Further features and advantages of this invention are more apparent in the description below, with reference to a preferred, non-limiting embodiment of a machine as illustrated in the accompanying drawings, in which.

DETAILED DESCRIPTION OF PREFERRED EMBODIMENTS OF THE INVENTION

Figure 1:
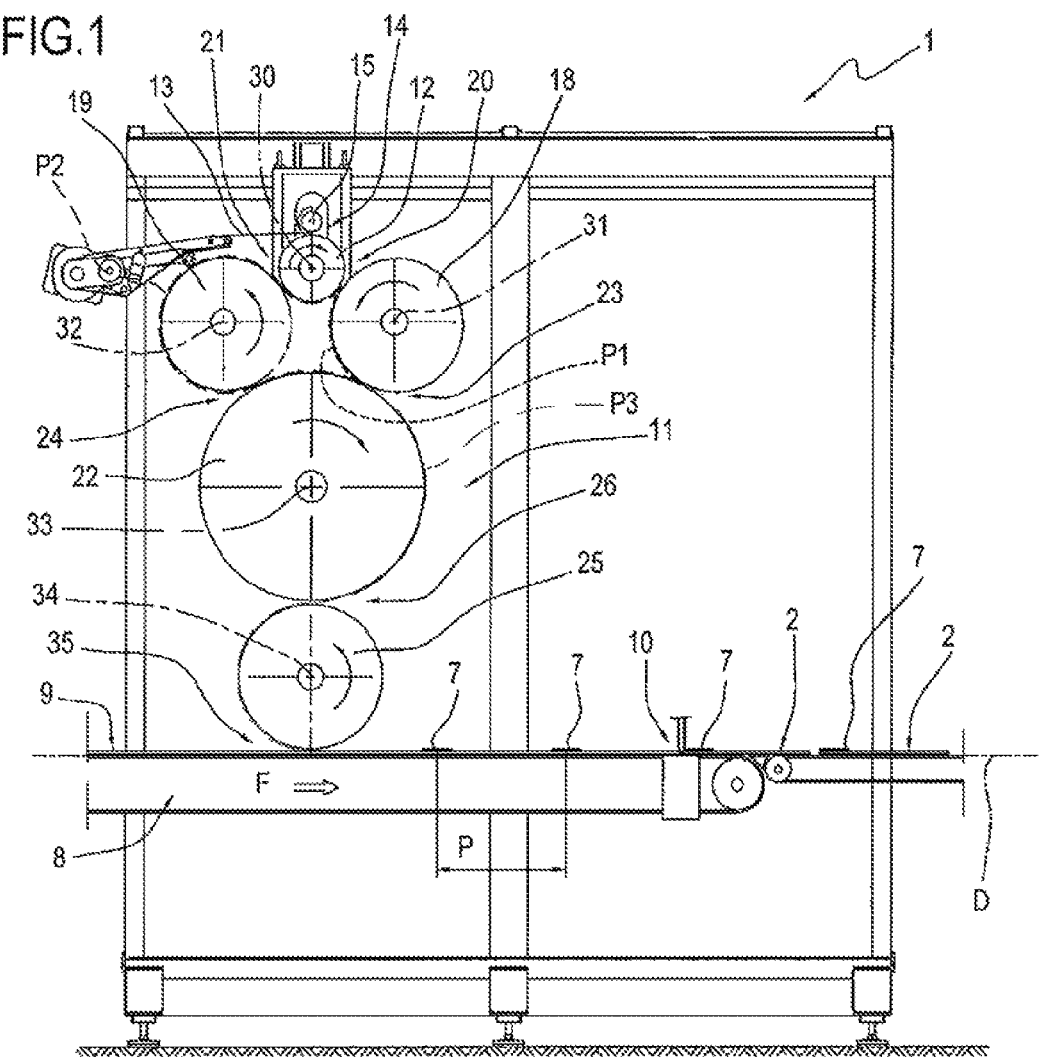
FIG. 1 is a schematic front view illustrating a machine for snaking absorbent sanitary articles according to this invention.

With reference to FIG. 1, the numeral 1 denotes in its entirety a machine for making absorbent sanitary articles 2.

Figure 2:
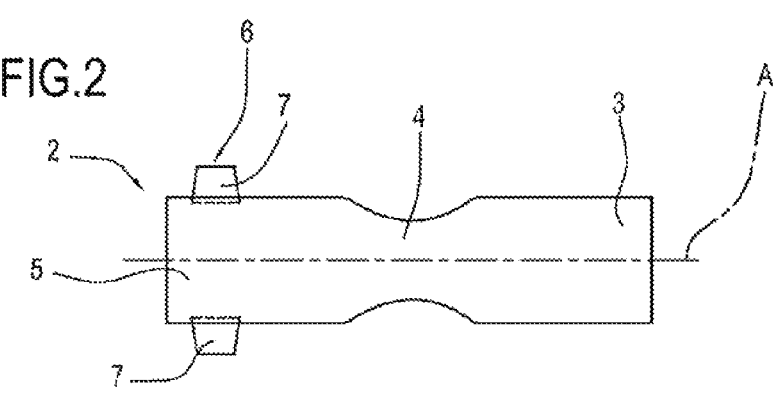
FIG. 2 is a schematic plan view of an absorbent sanitary article made by the machine according to the invention.

The absorbent sanitary article 2 has a substantially rectangular shape extending along a longitudinal axis A, as shown in FIG. 2, and comprises, in a line along the axis A, a front portion 3, a central portion 4 and a rear portion 5.

At its central portion 4, the absorbent article 2 comprises an internal absorbent padding, normally made from cellulose fibres, placed inside a soft container defined on one side by a permeable sheet of non-woven fabric and, on the other side, by an impermeable sheet of polyethylene.

The absorbent article 2 comprises at least one pair 6 of side tabs 7 which project from the rear portion 5 transversely to the axis A.

The side tabs 7 are, in use, designed to be placed over respective fastening zones of the front portion 3 in order to close the absorbent article 2 round the wearer's waist.

Preferably, the side tabs 7 are made of elastic material and have a surface which is partly covered with an adhesive substance, or provided with other quick fastening means to guarantee their fastening to the front portion 3 of the absorbent article 2.

The machine 1 for making absorbent sanitary articles comprises a feed line 8 for advancing a continuous web 9 of material for making the absorbent articles 2 and a cutting element 10 for cutting the continuous web 9 and by which the selfsame web 9 is divided into the individual absorbent articles 2.

The continuous web 9 advances along the feed line 8 in a direction D as indicated in FIG. 1 by the arrow F.

The machine 1 comprises a unit 11 for forming and applying at least one pair 6 of side tabs 7.

The forming and application unit 11 comprises a plurality of rollers 12, 18, 19, 22, 25 which rotate about respective axes 30, 31, 32, 33, 34 parallel to each other and to a direction transverse to the feed direction D of the continuous web 9.

Figure 3:
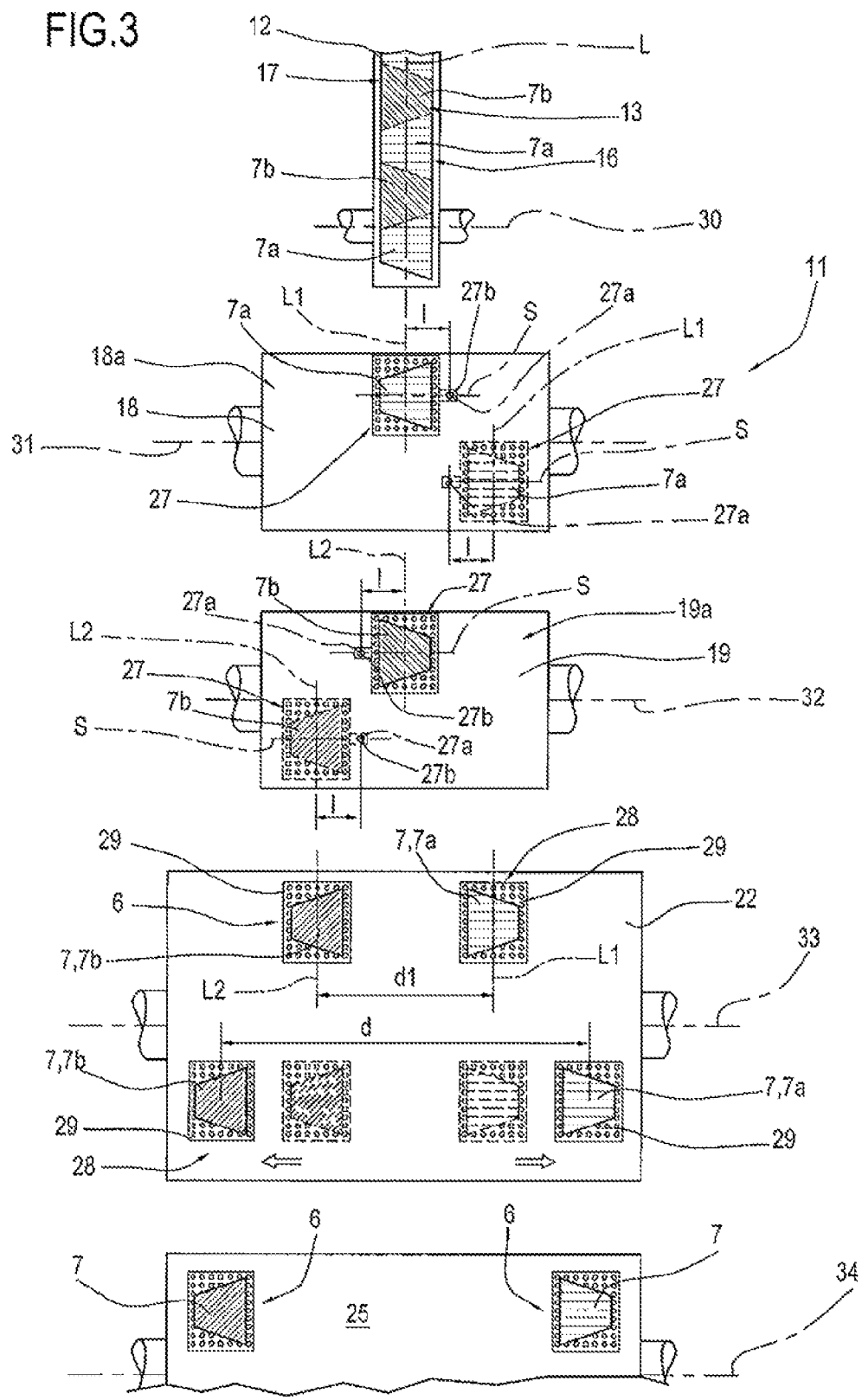
FIG. 3 schematically illustrates the operation of the machine of FIG. 1.
Figure 4:
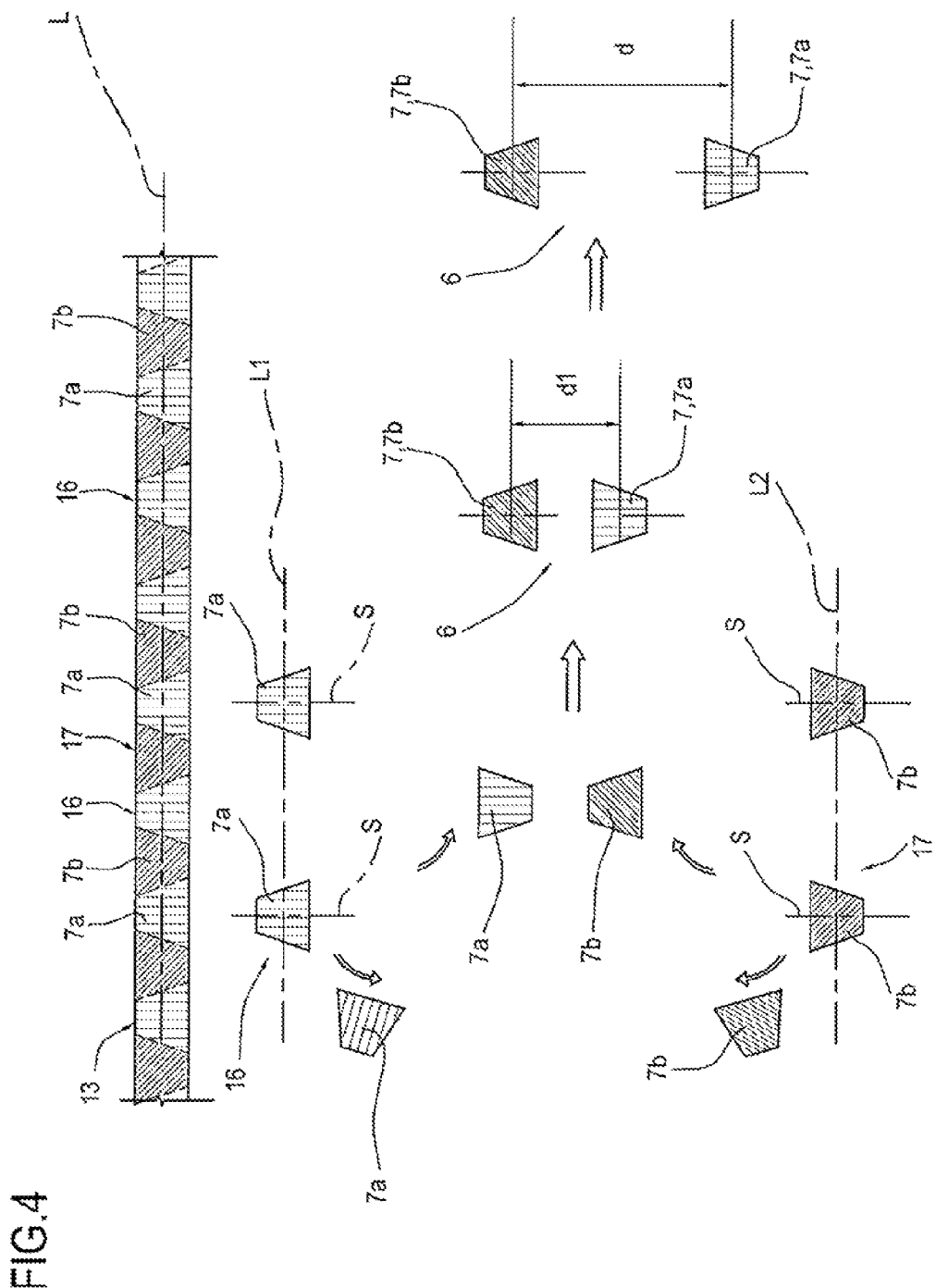
FIG. 4 schematically illustrates the steps in the making of the side tabs in the machine of FIG. 1.

More specifically, the forming and application unit 11 comprises a conveyor roller 12 for transporting a single continuous tape 13 with a longitudinal axis L—see FIGS. 3 and 4—towards a cutting station 14.

A cutting element 15 is located at the cutting station 14 and is opposed to the cylindrical outside surface of the conveyor roller 12.

The cutting element 15 acts in conjunction with the conveyor roller 12 to make on the continuous tape 13 a succession of oblique cuts transverse to the longitudinal axis L to divide the continuous tape 13 into a first and a second series 16 and 17 of side tabs 7.

The first and second series 16 and 17 of side tabs 7 are distinguished from each other in that the side tabs 7a of the first series 16 are oriented in the opposite direction to the side tabs 7b of the second series 17, relative to the longitudinal axis L.

More precisely, in the side tabs 7a of the first series 16, the longer longitudinal side, parallel to the longitudinal axis L, is on the right of the selfsame axis L, whereas in the side tabs 7b of the second series 17, the longer longitudinal side, parallel to the longitudinal axis L, is on the left of the selfsame axis L, as shown in FIGS. 3 and 4.

More specifically, the side tabs 7a and 7b of the first and second series 16 and 17 are symmetrical about an axis of symmetry S.

The axis of symmetry S is transversal to the longitudinal axis L.

A first and a second roller 18 and 19 for picking up the individual side tabs 7 are located downstream of the conveyor roller 12.

More specifically, the first and the second pickup roller 18 and 19 are tangent to the conveyor roller 12 at a respective first and second pickup station 20 and 21.

A roller 22 for forming pairs 6 of side tabs 7 is located downstream of the first and second pickup rollers 18 and 19.

The forming roller 22 is tangent to the first and the second pickup roller 18 and 19 at a respective first and second release station 23 and 24.

Lastly, an accelerator roller 25 is located downstream of the forming roller 22 and is capable of picking up the pairs 6 of side tabs 7 from the roller 22 itself in order to convey them in step and apply them to the continuous web 9.

More specifically, the accelerator roller 25 applies the pairs 6 of side tabs 7 according to a spacing P at an applicator station 35.

The forming roller 22 and the accelerator roller 25 are tangent at a transfer station 26 where the pairs 6 of side tabs 7 are transferred.

The first and second pickup rollers 18 and 19 each comprise a respective set of pads 27 for retaining the side tabs 7.

The pads 27 are located on the cylindrical outside surfaces 18a and 19a of the first and second rollers 18 and 19, respectively, and are angularly equispaced.

Preferably, the pads 27 retain the side tabs 7 by suction.

In order to orient the individual side tabs 7a and 7b of the first and second series 16 and 17, respectively, so as to form a pair 6 of side tabs 7, the retaining pads 27 rotate about a respective axis of rotation 27a.

Each pad 27 comprises a pin 27b which is hinged to the respective first and second pickup roller 18 and 19 and which rotates about the axis of rotation 27a.

In the embodiment illustrated, the axis of rotation 27a of the pin 27b is clear of the free surface by which the individual side tab 7a and 7b is picked up.

Further, the axis of rotation 27a of the pin 27b is transverse to the axis of rotation 31 and 32 of the respective first and second pickup roller 18 and 19.

More precisely, the axis of rotation 27a is located along a direction substantially radial to the respective pickup roller 18 and 19.

Thus, as it rotates about its axis 27a, the pin 27b supports the respective pad 27 in cantilever fashion.

It should be noted that, as illustrated in FIG. 3, the 180° rotation of each pad 27 about the respective axis of rotation 27a (arrow F) causes the corresponding tab 7 to rotate.

Consequently, following a 180° rotation about the axis of rotation 27a of each pad 27, the respective side tab 7a and 7b adopts a substantially mirror symmetric position relative to the position adopted before the pad 27 was rotated.

Preferably, in an embodiment not illustrated, the pins 27b of each pad 27 are driven in rotation by cam profiles (not illustrated)

Figure 5:
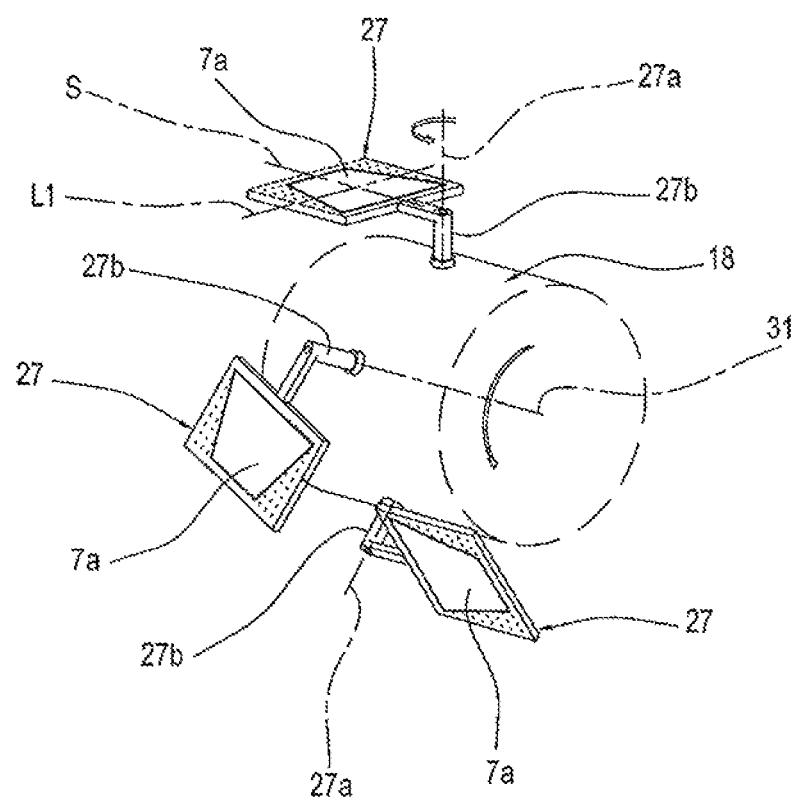
FIG. 5 is a perspective view of one of the pickup rollers of the machine illustrated in FIG. 1.

As illustrated in FIGS. 3 and 5, the retaining pads 27, by turning about their axes 27a by 180°, pass from a first pickup position, drawn with a continuous line in FIG. 3, to a second release position, drawn with a dashed line in FIG. 3.

It should be noted that each pad, besides rotating by 180°, advances by a defined stretch as a result of the turning of the corresponding pickup roller 17 and 18.

More specifically, both in the pickup position and in the release position, the axis of symmetry S of side tab 7 positioned on the retaining pad 27 is parallel to the axis of rotation 31, 32 of the respective first and second pickup roller 18 and 19.

With reference to FIG. 3, the first pickup roller 18, through the agency of its pads 27, receives the individual side tabs 7a of the first series 16 at the first pickup station 20.

More specifically, at the aforementioned pickup position, a longitudinal axis L1 of the side tab 7a of the first series 16 is located at a distance "I", from the axis of rotation 27a, in a direction parallel to the axis of rotation 31 of the pickup roller 18.

At the pickup position, the longitudinal axis L1 of the side tab 7a is substantially aligned with the longitudinal axis of extension L of the continuous tape 13.

In the particular case illustrated by way of an example, the axis L1 is perpendicular to the axis of symmetry S of the side tab 7.

Consequently, the longer longitudinal side of each side tab 7a is located on the right of the longitudinal axis L1.

At the release position of each pad 27, after being rotated by 180° about its axis 27a, each side tab 7a of the first series 16 is positioned with its axis of symmetry S parallel to the axis of rotation 31 of the first pickup roller 18 and with its longer longitudinal side located on the left of the longitudinal axis L1 of the selfsame side tab 7a.

Thus, as stated above, the side tab 7a of the first series 16 adopts, at the release position of the pad 27, a substantially mirror symmetric position relative to the pickup position of the selfsame pad 27.

The second pickup roller 19, through the agency of its pads 27, receives the individual side tabs 7b of the second series 17 at the second pickup station 21.

More specifically, at the aforementioned pickup position, a longitudinal axis L2 of the side tab 7b of the second series 17 is located at a distance "I", from the axis of rotation 27a, in a direction parallel to the axis of rotation 32 of the pickup roller 19.

At the pickup position of each pad 27, the longitudinal axis L2 of the side tab 7b is substantially aligned with the longitudinal axis of extension L of the continuous tape 13.

At the release position of each pad 27, after being rotated by 180° about its axis 27a, each side tab 7b of the second series 17 is positioned with its axis of symmetry S parallel to the axis of rotation 32 of the second pickup roller 19 and with its longer longitudinal side located on the right of the longitudinal axis L2 of the selfsame side tab 7b.

Thus, as stated above, the side tab 7b of the second series 17 adopts, at the release position of the pad 27, a substantially mirror symmetric position relative to the pickup position of the selfsame pad 27.

It should be noted that the side tabs 7a and 7b of the first and second series 16 and 17 in the release position are correctly oriented to form a pair 6 of side tabs 7.

Since the axis of rotation 27a of the pad 27 is at a distance "I" from the longitudinal axis L1 and L2 of the respective side tab 7a and 7b, rotating each pad 27 causes the side tabs 7a and 7b to move in a direction parallel to the axis of rotation 31, 32 of the first and the second pickup roller 18 and 19.

The first movement of the side tabs 7a and 7b is thus a result of rotating each pad 27 about its axis 27a.

More specifically, the side tabs 7a and 7b are moved sideways by a distance equal to twice the distance "I".

Thus, when the first and second pickup rollers 18 and 19 deliver the side tabs 7a and 7b to the roller 22 for forming the pairs 6, the side tabs are spaced from each other by an initial reciprocal distance d1.

The initial reciprocal distance d1 is equal to the distance between the longitudinal axes L1 and L2 of the tabs 7a and 7b after the pads 27 have been rotated about their respective axes of rotation 27a.

In the embodiment described, the distance d1 is equal to four times the defined distance "I".

The initial distance d1 may be less than, greater than, or equal to the final reciprocal distance d which is predetermined based on the waistline of the absorbent article 2.

in the embodiment illustrated, the initial distance d1 is less than the final reciprocal distance d.

In effect, in order to space the side tabs 7 of each pair 6 further from each other, the roller 22 for forming the pairs 6 of side tabs 7 comprises pairs 28 of slidable pads 29 on its cylindrical outside surface.

At least one of the slidable pads 29 of each pair 28 is movable in a direction parallel to the axis of rotation 33 of the forming roller 22, positioning the side tabs 7 of each pair 6 at a final reciprocal distance d.

Preferably, the slidable pads 29 are both slidable in parallel with the axis of rotation 33 of the forming roller 22, one in one direction and the other in the opposite direction.

In other words, the roller 22 for forming the pairs 6 translates the side tabs 7 of each pair 6 from an initial distance d1 equal to the reciprocal distance at which the side tabs 7 are delivered to the forming roller 22 to a distance d equal to the predetermined final reciprocal distance.

More specifically, in the embodiment described, the roller 22 for forming the pairs 6 translates the side tabs 7 of each pair 6 in such a way as to increase the reciprocal distance between them until reaching the final distance d.

Alternatively, if the initial distance d1 is greater than the final distance d, the roller 22 for forming the pairs 6 translates the side tabs 7 of each pair 6 in such a way as to decrease the reciprocal distance between them until reaching the final distance d.

In a further variant embodiment, if the initial distance d1 is equal to the final distance d, the roller 22 for forming the pairs 6 simply conveys the side tabs 7 of each pair 6 without translating them.

In use, once the continuous tape 13 has been cut by the succession of oblique cuts into the first and second series 16 and 17 of side tabs 7, the side tabs 7a of the first series 16 are conveyed along a first path P1 and the side tabs 7b of the second series 17 are conveyed along second path P2, distinct from the first path P1.

More specifically, the first path P1 extends from the first pickup station 20 of the first roller 18 to the first release station 23.

The second path P2 extends from the second pickup station 21 of the second roller 19 to the first release station 23 of the first roller 18, passing through the second release station 24.

Once the side tabs 7a and 7b of the first and second series 16 and 17 have formed a pair 6 on the forming roller 22, the paired tabs travel along a common third path P3 which extends from the first release station 23 until the pairs 6 are applied to the continuous web 9.

The retaining pads 27 of the first and second pickup rollers 18 and 19 retain and rotate the side tabs 7a, 7b, in the plane which the side tabs 7a, 7b themselves lie in, along the first and second paths P1 and P2, orienting them correctly to form a pair 6.

The roller 22 for forming the pairs 6 receives a side tab 7a of the first series 16 from the first pickup roller 18 and a side tab 7b of the second series 17 from the second pickup roller 19, forming respective pairs 6 of side tabs 7 to be suitably applied to the continuous web 9 according to the spacing P.

During the rotation of the roller 22 for forming the pairs 6, the slidable pads 29 translate the side tabs 7 of each pair 6 along a direction parallel to the axis 33 until they reach the predetermined final reciprocal distance d.

The accelerator roller 25, located downstream of the roller 22 for forming the pairs 6, picks up the pairs 6 of side tabs 7, after they have been oriented and correctly spaced, conveys them according to the spacing P and applies them to the continuous web 9.

It should be noted that the first and the second pickup roller 18 and 19 may be accelerator rollers designed to slow down while they pick up the respective side tabs 7a and 7b from the conveyor roller 12 at the respective first and second release station 20 and 21, and to speed up in the stretch from the first and the second pickup station 20 and 21 to the respective first and second release station 23 and 24 of the forming roller 22, along the respective paths P1 and P2.

Advantageously, the rollers 12, 18, 19, 22, 25 of the forming and application unit 11 rotate at a higher speed than in the prior art, thereby allowing the productivity of the machine 1 to be increased.

This is made possible by the retaining pads 27 which rotate about their axes 27a, thus allowing the rotation speed of the first and second pickup rollers 18 and 19 to be increased.

Advantageously, the rotating retaining pads 27 rotate the side tabs 7, in order to orient them correctly, and simultaneously translate each individual side tab 7 in a direction parallel to the axis of rotation 31 and 32 of the first and the second pickup roller 18 and 19, given the distance "I" between the longitudinal axis L1 and L2 of the side tabs 7 and the axis of rotation 27a of each pad 27 along a direction parallel to the axis of rotation 31, 32 of the respective pickup roller 17, 18.

The invention claimed is:

1. A method for making absorbent sanitary articles whereby each absorbent sanitary article is provided with at least one pair of side tabs, comprising:
   feeding a single continuous tape with a longitudinal axis towards a cutting station where the single continuous tape is divided, by a succession of oblique cuts transverse to the longitudinal axis, into a first and a second series of side tabs where the side tabs of the first series are oriented in an opposite direction to the side tabs of the second series, relative to the longitudinal axis;
   feeding the side tabs of the first series along a first path, starting from a first pickup station located downstream of the cutting station;
   feeding the side tabs of the second series along a second path, separate from the first path, starting from a second pickup station located downstream of the first pickup station;
   rotating the side tabs of the first series by 180° about an axis of rotation as they feed along the first path;
   rotating the side tabs of the second series by 180° about an axis of rotation as they feed along the second path;
   combining the rotated side tabs of the first and second series, transferring the rotated side tabs of the first and second series separately along a third, common path along which each tab of the first series has a respective tab of the second series placed alongside to form a pair of side tabs;
   applying each pair of side tabs, according to a predetermined spacing, to a continuous web of material for making the absorbent sanitary articles.

2. The method according to claim 1, wherein the side tabs of the first and second series have a respective longitudinal axis situated at a defined distance from the respective axis of rotation.

3. The method according to claim 2, wherein after the side tabs of the first series and of the second series have been rotated by 180° about the respective axes, of rotation, the side tabs of the first series and of the second series are displaced sideways by a distance equal to twice the defined distance between the respective longitudinal axis and the axis of rotation.

4. The method according to claim 3, wherein at least one of the side tabs of each pair is translated sideways while the pairs are being fed along the third path starting from an initial reciprocal distance until reaching a final reciprocal distance determined by a waistline of the absorbent sanitary article.

5. The method according to claim 2, wherein at least one of the side tabs of each pair is translated sideways while the pairs are being fed along the third path starting from an initial reciprocal distance until reaching a final reciprocal distance determined by a waistline of the absorbent sanitary article.

6. The method according to claim 1, wherein at least one of the side tabs of each pair is translated sideways while the pairs are being fed along the third path starting from an initial reciprocal distance until reaching a final reciprocal distance determined by a waistline of the absorbent sanitary article.

7. A machine for making absorbent sanitary articles, comprising:
   a feed line for advancing a continuous web of material for making the absorbent sanitary articles,
   a cutting element for cutting the continuous web into individual absorbent sanitary articles,
   a forming and applying unit for forming and applying at least one pair of side tabs of the absorbent sanitary articles;
   the forming and application unit comprising a plurality of rollers which rotate about respective axes parallel to a transverse direction, relative to a feed direction of the continuous web, and which plurality of rollers comprise:
      a conveying roller for conveying a single continuous tape with a longitudinal axis towards a cutting station and a cutting element acting in conjunction with the conveying roller for making on the single continuous tape a succession of oblique cuts transverse to the longitudinal axis to divide the single continuous tape into a first and a second series of side tabs where the side tabs of the first series are oriented in the opposite direction to the side tabs of the second series, relative to the longitudinal axis;
      a first pickup roller and a second pickup roller for picking up the side tabs of the side tabs of the first and second series, respectively, at a first pickup station and a second pickup station, both located downstream of the cutting station;
      a forming roller for forming the pairs of side tabs and located downstream of the first and second pickup rollers; the forming roller receiving a side tab of the first series and a side tab of the second series to form respective pairs of side tabs to be applied to the continuous web at a spacing,
      the first and second pickup rollers each including respective pads for retaining the side tabs; the pads rotating by 180° about a respective axis of rotation situated along a radial direction of the first and second pickup rollers and transverse to the axes of rotation of the first and second pickup rollers.

8. The machine according to claim 7, wherein each side tab of the first and second series has a respective longitudinal axis; the axis of rotation of the pad is situated at a defined distance from the longitudinal axis of the respective side tab, along a direction parallel to the axes of rotation of the first and second pickup rollers.

9. The machine according to claim 8, wherein each retaining pad of the first and second pickup rollers rotates by 180° about an axis of the each retaining pad; each retaining pad passing from a position where of picking up the respective side tab to a release position where the side tabs are mirror symmetric relative to their pickup positions and displaced sideways by a distance equal to twice the defined distance between the axis of rotation and the longitudinal axis of the respective side tab, along a direction parallel to the axes of rotation of the first and second pickup rollers.

10. The machine according to claim 8, and further comprising an accelerator roller, located downstream of the forming roller for picking up the pairs of oriented and spaced side tabs, conveying the pairs stepwise and applying the pairs to the continuous web.

11. The machine according to claim 8, wherein the first and second pickup rollers are accelerator rollers configured to decelerate at the respective first and second pickup station and accelerate in a stretch between the first and second pickup station and a respective first and second release station.

12. The machine according to claim 9, wherein the forming roller comprises slidable pads movable along a direction parallel to an axis of rotation of the forming roller; the slidable pads moving the side tabs of each pair from an initial reciprocal distance to a final reciprocal distance determined by a waistline of the absorbent sanitary article.

13. The machine according to claim 9, and further comprising an accelerator roller, located downstream of the forming roller for picking up the pairs of oriented and spaced side tabs, conveying the pairs stepwise and applying the pairs to the continuous web.

14. The machine according to claim 9, wherein the first and second pickup rollers are accelerator rollers configured to decelerate at the respective first and second pickup station and accelerate in a stretch between the first and second pickup station and a respective first and second release station.

15. The machine according to claim 7, wherein the forming roller comprises slidable pads movable along a direction parallel to an axis of rotation of the forming roller; the slidable pads moving the side tabs of each pair from an initial reciprocal distance to a final reciprocal distance determined by a waistline of the absorbent sanitary article.

16. The machine according to claim 15, and further comprising an accelerator roller, located downstream of the forming roller for picking up the pairs of oriented and spaced side tabs, conveying the pairs stepwise and applying the pairs to the continuous web.

17. The machine according to claim 15, wherein the first and second pickup rollers are accelerator rollers configured to decelerate at the respective first and second pickup station and accelerate in a stretch between the first and second pickup station and a respective first and second release station.

18. The machine according to claim 7, and further comprising an accelerator roller, located downstream of the forming roller for picking up the pairs of oriented and spaced side tabs, conveying the pairs stepwise and applying the pairs to the continuous web.

19. The machine according to claim 7, wherein the first and second pickup rollers are accelerator rollers configured to decelerate at the respective first and second pickup station and accelerate in a stretch between the first and second pickup station and a respective first and second release station.

20. The machine according to claim 8, wherein the forming roller comprises slidable pads movable along a direction parallel to an axis of rotation of the forming roller; the slidable pads moving the side tabs of each pair from an initial reciprocal distance to a final reciprocal distance determined by a waistline of the absorbent sanitary article.

* * * * *